US008007858B2

(12) United States Patent
Pacetti et al.

(10) Patent No.: US 8,007,858 B2
(45) Date of Patent: *Aug. 30, 2011

(54) SYSTEM AND METHOD FOR COATING IMPLANTABLE DEVICES

(75) Inventors: Stephen D. Pacetti, San Jose, CA (US); Wouter E. Roorda, Palo Alto, CA (US); Ni Ding, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/363,538

(22) Filed: Jan. 30, 2009

(65) Prior Publication Data

US 2009/0136556 A1    May 28, 2009

Related U.S. Application Data

(63) Continuation of application No. 10/040,538, filed on Dec. 28, 2001, now Pat. No. 7,504,125, which is a continuation-in-part of application No. 09/894,293, filed on Jun. 27, 2001, now abandoned, which is a continuation-in-part of application No. 09/844,522, filed on Apr. 27, 2001, now Pat. No. 6,818,247.

(51) Int. Cl.
*A61L 33/00* (2006.01)

(52) U.S. Cl. ............... 427/2.24; 428/36.91; 428/412; 428/423.1; 428/474.4; 428/480; 428/500; 427/2.25; 427/2.28; 427/2.3; 427/286; 427/287

(58) Field of Classification Search .............. 428/412; 264/8; 427/2.3, 2.24, 2.25, 2.28, 261, 286, 427/287

See application file for complete search history.

(56) References Cited

U.S. PATENT DOCUMENTS

| 2,072,303 | A | | 3/1937 | Herrmann et al. |
|---|---|---|---|---|
| 3,882,816 | A | | 5/1975 | Rooz et al. |
| 3,995,075 | A | | 11/1976 | Cernauskas et al. |
| 4,269,713 | A | | 5/1981 | Yamashita et al. |
| 4,323,524 | A | * | 4/1982 | Snowden ............ 264/8 |
| 4,560,374 | A | | 12/1985 | Hammerslag |
| 4,733,665 | A | | 3/1988 | Palmaz |
| 4,800,882 | A | | 1/1989 | Gianturco |
| 4,839,055 | A | | 6/1989 | Ishizaki et al. |
| 4,865,879 | A | | 9/1989 | Finlay |
| 4,886,062 | A | | 12/1989 | Wiktor |

(Continued)

FOREIGN PATENT DOCUMENTS

EP    0 665 023    8/1995

(Continued)

OTHER PUBLICATIONS

Barath et al., *Low Dose of Antitumor Agents Prevents Smooth Muscle Cell Proliferation After Endothelial Injury*; JACC vol. 13, No. 2; Feb. 1989:252A (Abstract).

(Continued)

*Primary Examiner* — Dah-Wei D Yuan
*Assistant Examiner* — Andrew Bowman
(74) *Attorney, Agent, or Firm* — Squire, Sanders & Demsey (US) LLP

(57) ABSTRACT

A method and system of coating an implantable device, such as a stent, are provided.

30 Claims, 15 Drawing Sheets

U.S. PATENT DOCUMENTS

| | | | |
|---|---|---|---|
| 4,977,901 A | 12/1990 | Ofstead | |
| 5,112,457 A | 5/1992 | Marchant | |
| 5,328,471 A | 7/1994 | Slepian | |
| 5,455,040 A | 10/1995 | Marchant | |
| 5,464,650 A | 11/1995 | Berg et al. | |
| 5,558,900 A | 9/1996 | Fan et al. | |
| 5,578,073 A | 11/1996 | Haimovich et al. | |
| 5,605,696 A | 2/1997 | Eury et al. | |
| 5,628,730 A | 5/1997 | Shapland et al. | |
| 5,667,767 A | 9/1997 | Greff et al. | |
| 5,670,558 A | 9/1997 | Onishi et al. | |
| 5,700,286 A | 12/1997 | Tartaglia et al. | |
| 5,716,981 A | 2/1998 | Hunter et al. | |
| 5,800,392 A | 9/1998 | Racchini | |
| 5,824,049 A | 10/1998 | Ragheb et al. | |
| 5,830,178 A | 11/1998 | Jones et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,865,814 A | 2/1999 | Tuch | |
| 5,873,904 A | 2/1999 | Ragheb et al. | |
| 5,891,507 A | 4/1999 | Jayaraman | |
| 5,971,954 A | 10/1999 | Conway et al. | |
| 5,980,928 A | 11/1999 | Terry | |
| 5,980,972 A | 11/1999 | Ding | |
| 6,010,530 A | 1/2000 | Goicoechea | |
| 6,015,541 A | 1/2000 | Greff et al. | |
| 6,030,371 A | 2/2000 | Pursley | |
| 6,042,875 A | 3/2000 | Ding et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,080,488 A | 6/2000 | Hostettler et al. | |
| 6,083,257 A | 7/2000 | Taylor et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,113,629 A | 9/2000 | Ken | |
| 6,120,536 A | 9/2000 | Ding et al. | |
| 6,120,904 A | 9/2000 | Hostettler et al. | |
| 6,121,027 A | 9/2000 | Clapper et al. | |
| 6,129,761 A | 10/2000 | Hubbell | |
| 6,146,688 A * | 11/2000 | Morgan et al. | 427/2.3 |
| 6,153,252 A | 11/2000 | Hossainy et al. | |
| 6,156,373 A | 12/2000 | Zhong et al. | |
| 6,165,212 A | 12/2000 | Dereume et al. | |
| 6,306,176 B1 | 10/2001 | Whitbourne | |
| 6,358,556 B1 | 3/2002 | Ding et al. | |
| 6,358,567 B2 | 3/2002 | Pham et al. | |
| 6,364,903 B2 | 4/2002 | Tseng et al. | |
| 6,368,658 B1 | 4/2002 | Schwarz et al. | |
| 6,395,326 B1 * | 5/2002 | Castro et al. | 427/2.24 |
| 6,407,009 B1 | 6/2002 | You et al. | |
| 6,426,145 B1 * | 7/2002 | Moroni | 428/412 |
| 6,503,954 B1 | 1/2003 | Bhat et al. | |
| 6,534,112 B1 | 3/2003 | Bouchier et al. | |
| 6,555,157 B1 | 4/2003 | Hossainy | |
| 6,818,247 B1 * | 11/2004 | Chen et al. | 427/2.24 |
| 7,504,125 B1 * | 3/2009 | Pacetti et al. | 427/2.24 |

FOREIGN PATENT DOCUMENTS

| | | |
|---|---|---|
| EP | 0 970 711 | 1/2000 |
| WO | WO 91/12846 | 9/1991 |
| WO | WO 97/45105 | 12/1997 |
| WO | WO 99/63981 | 12/1999 |
| WO | WO 00/02599 | 1/2000 |
| WO | WO 00/12147 | 3/2000 |
| WO | WO 00/64506 | 4/2000 |
| WO | WO 01/01890 | 1/2001 |
| WO | WO 01/45763 | 6/2001 |

OTHER PUBLICATIONS

Dichek et al., *Seeding of Intravascular Stents With Genetically Engineered Endothelial Cells*, Circulation 1989; 1347-1353.

Forester et al., *A Paradigm for Restenosis Based on Cell Biology: Clues for the Development of New Preventive Therapies*; J. Am. Coll. Cardio. 1991; 17:758-769.

Matsumaru et al.; *Embolic Materials for Endovascular Treatment of Cerebral Lesions*; J. Biomatter Sci. Polymer Edn., vol. 8, No. 7 (1997) pp. 555-569.

Miyasaki et al., *Antitumor Effect of Implanted Ethylene-Vinyl Alcohol Copolymer Matrices Containing Anticancer Agents on Ehrlich Ascites Carcinoma and P388 Leukemia in Mice*; Chem. Pharm. Bull. 33(6) (1985) pp. 2490-2498.

Miyazawa et al., *Effects of Pemirolast and Tranilast on Intimal Thickening After Arterial Injury in the Rat*; J. Cardiovasc. Pharmacol. (1997) pp. 157-162.

Ohsawa et al., *Preventive Effects of an Antiallergic Drug, Pemirolast Potassium, on Restenosis After Percutaneous Transluminal Coronary Angioplasty*; American Heart Journal (1998) pp. 1081-1087.

Shigeno, *Prevention of Cerebrovascular Spasm by Bosentan, Novel Endothelin Receptor*; Chemical Abstract 125:212307 (1996).

\* cited by examiner

SYSTEM AND METHOD FOR COATING IMPLANTABLE DEVICES

CROSS-REFERENCE

This application is a continuation of application Ser. No. 10/040,538, filed on Dec. 28, 2001, and is now an issued patent, U.S. Pat. No. 7,504,125, which is a continuation-in-part of application Ser. No. 09/894,293, which was filed on Jun. 27, 2001 and is now abandoned, which is a continuation-in-part of application Ser. No. 09/844,522, which was filed on Apr. 27, 2001 and is now an issued U.S. Pat. No. 6,818,247. The disclosure of all three application Ser. Nos. 10/040,538, 09/894,293, and 09/844,522, are incorporated by reference herein, as if fully set forth, including any drawings.

BACKGROUND OF THE INVENTION

1. Field of the Invention

This invention relates to a method and system for coating an implantable device, such as a stent.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

A shortcoming of the above-described method of medicating a stent is the potential for coating defects due to the large amount of liquid composition applied to the relatively small surface area of the stent. The liquid composition can flow, wick, and collect as the amount of composition on the stent increases during the coating process. As the solvent evaporates, the excess composition hardens, leaving the excess coating as clumps or pools on the struts or webbing between the struts.

Another shortcoming of the above-described method of medicating a stent is the potential for loss of the therapeutic substance from the coating or production of a coating that does not provide for a suitable residence time of the substance at the implanted region. Initial portions of a liquid composition containing a therapeutic substance sprayed onto a stent adhere to the stent surface. However, as the liquid composition continues to be applied to the stent, layers of the composition are formed on top of one another. When exposed to the solvent in the upper layers, the therapeutic substance in the lower layers can be re-dissolved into the upper layers of the composition or extracted out from the coating. Having the therapeutic substance maintained in merely the upper regions of the coating provides for a short residence time of the substance at the implanted region, as the therapeutic substance will be quickly released. Prolonged residence times may be desirable for a more effective treatment of a patient.

The present invention addresses such problems by providing a method and system for coating implantable devices.

SUMMARY OF THE INVENTION

In accordance with one aspect of the invention, a method of coating an implantable device is disclosed including applying a composition including a solvent to an implantable device and directing a gas onto the implantable device, wherein if the solvent has a vapor pressure greater than 17.54 Torr at ambient temperature the temperature of the gas is adjusted to inhibit the evaporation of the solvent, and if the solvent has a vapor pressure of less than 17.54 Torr at ambient temperature the temperature of the gas is adjusted to induce the evaporation of the solvent.

In one embodiment of the present invention, the implantable device is a radially expandable stent. In another embodiment, the composition is applied simultaneous with the directing of the gas. In a further embodiment, the composition includes a polymer dissolved in the solvent and optionally an active agent added thereto.

In accordance with a further aspect of the present invention, a method of coating an implantable device is disclosed including applying a composition including a solvent to an implantable device, and directing a gas onto the implantable device simultaneous with application of the composition, to either induce or inhibit evaporation of the solvent from the composition to form a coating on the implantable device, wherein if the solvent is non-volatile the temperature of the gas is adjusted to induce the evaporation of the solvent, and if the solvent is volatile the temperature of the gas is adjusted to inhibit the evaporation of the solvent.

In one embodiment, the method also includes that if the solvent is non-volatile increasing the temperature of the composition to a temperature above ambient temperature prior to application of the composition onto the implantable device, or alternatively, if the solvent is volatile decreasing the temperature of the composition to a temperature below ambient temperature prior to application of the composition onto the implantable device.

In a further aspect, a system for spraying a coating onto an implantable device is disclosed including a sprayer for applying a composition including a solvent on an implantable device, and a blower for directing a gas onto the implantable device, wherein if the solvent has a vapor pressure greater than 17.54 Torr at ambient temperature the temperature of the gas is adjusted to inhibit the evaporation of the solvent, and if the solvent has a vapor pressure of less than 17.54 Torr at ambient temperature the temperature of the gas is adjusted to induce the evaporation of the solvent.

In one embodiment, the sprayer includes a temperature controller for adjusting the temperature of the composition.

DETAILED DESCRIPTION

For ease of discussion, the systems and methods detailed herein will be described with reference to coating a stent. However, the device or prosthesis coated in accordance with embodiments of the present invention may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

System for Coating the Device

Figure 1:
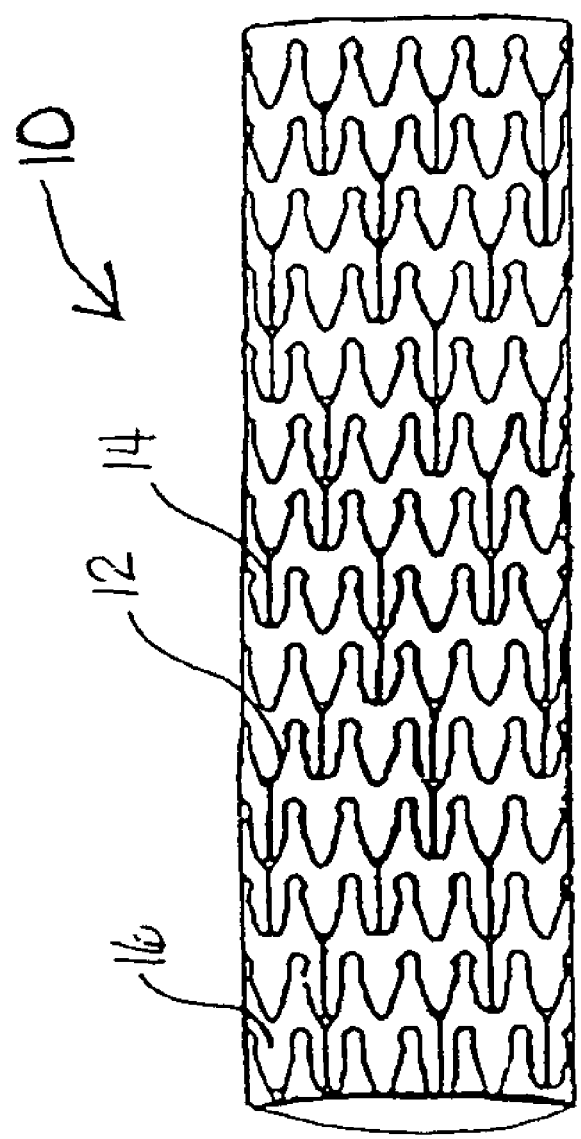
FIG. 1 illustrates a conventional stent.
Figure 2:
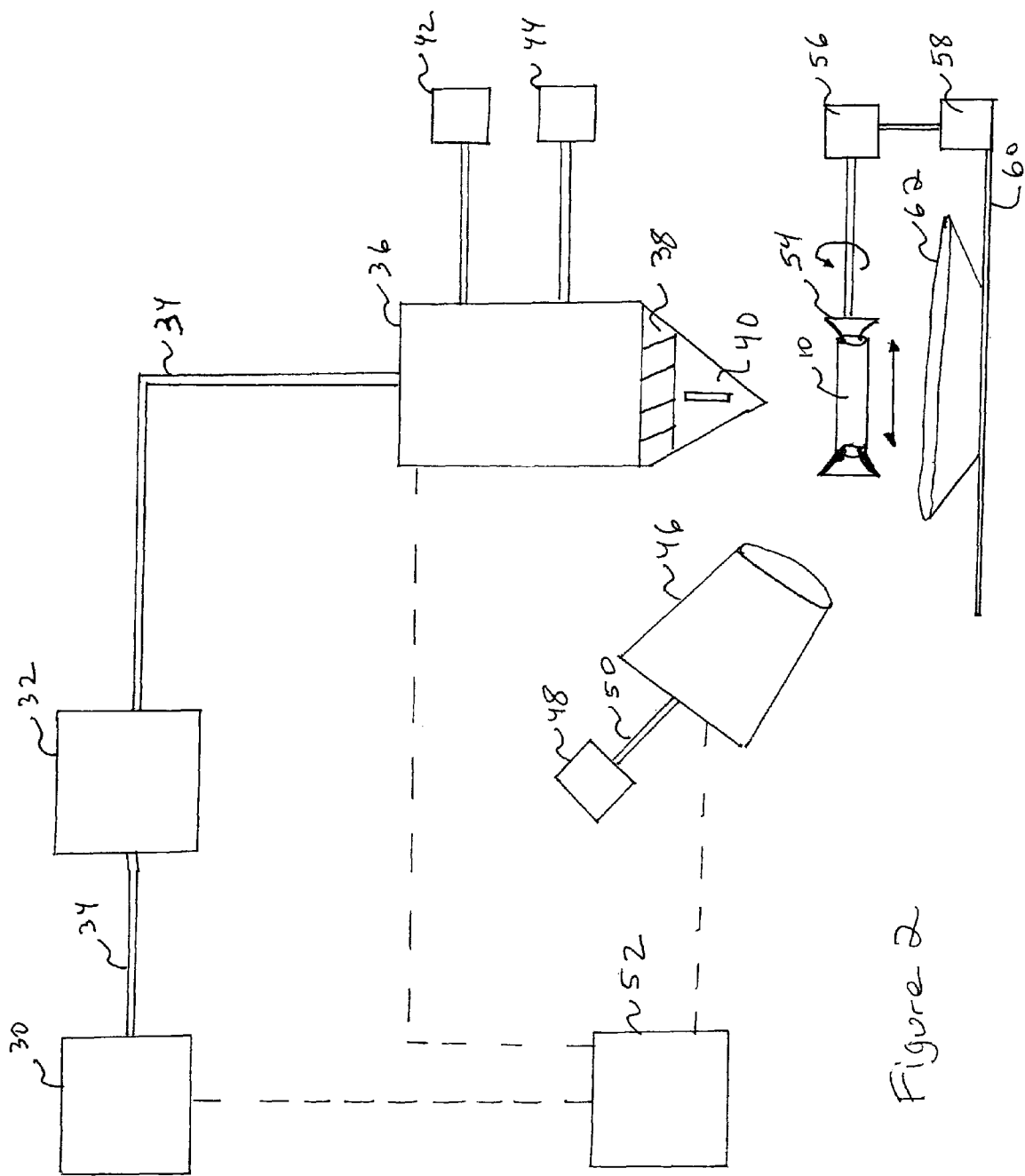
FIG. 2 illustrates a coating system for forming a coating on a stent.

An embodiment of a system for spray coating is depicted in FIG. 2. Referring to FIG. 2, an air pump 30 can provide air pressure to a reservoir 32 through a conduit 34. Reservoir 32 can hold a solution which includes a polymer and a solvent, and optionally an active agent. The air pressure delivered from air pump 30 should be sufficient to feed the solution in reservoir 32 into a sprayer 36 via conduit 34. Instead of air pump 30, the system may include a continuous feed pump (e.g., a syringe pump) to provide pressure to reservoir 32.

Sprayer 36 can be a commercially available apparatus, such as the EFD 780S spray device with a VALVEMATE 7040 control system (manufactured by EFD Inc., East Providence, R.I.). The EFD 780S spray device is an air-assisted external mixing atomizer. The composition is atomized into small droplets by air and uniformly applied to the stent surfaces. Other types of spray applicators, including air-assisted internal mixing atomizers and ultrasonic applicators, can also be used for the application of the composition.

As the solution enters the chamber of sprayer 36, a temperature controller 38 can be used for adjusting the temperature of the composition to a temperature other than ambient temperature. Temperature controller 38 can be positioned in close proximity to a nozzle 40 of sprayer 36. Such placement of temperature controller 38 allows for the heating of nozzle 40 at a concentrated area so as to prevent prolong exposure of the drug solution to the heat, which for heat sensitive drugs such as actinomycin D, could prevent the degradation of the drug. The temperature of the composition can be adjusted contemporaneously with the spraying of the composition from sprayer 36. Temperature controllers or thermal blocks are commercially available. One commercial example of a temperature controller is EUROTHERM (model 2416) (Eurotherm Control, Inc., Leesburg, Va.). In another example, the temperature of the composition can be adjusted at reservoir 32.

As the solution enters the chamber of sprayer 36, the solution is exposed to pressurized air from atomizing gas source 42. Atomizing gas source 42 can provide enough gas (e.g., air) so that the fluid is converted into a mist-like state. Sprayer 36 can also be in communication with an actuating gas source 44 which controls a precision needle valve (not shown) that controls the flow of the coating solution out of nozzle 40. The precision needle valve allows the solution flow to start and stop cleanly without the formation of drips, which could fall onto stent 10, and without solution accumulation at nozzle 40, which may cause clogging. Nozzle 40 may be oriented at any angle relative to the longitudinal axis of the stent. The angle can range from parallel to perpendicular orientation. Nozzle 40 can be either stationary or movable in a parallel and/or perpendicular direction relative to the longitudinal axis of stent 10, or can rotate around the axis of stent 10. The distance from the tip of nozzle 40 to the outer surface of stent 10 can be from about 0.5 cm to about 5.0 cm, more narrowly from about 1.0 cm to about 2.0 cm.

The present invention can also include a blower 46 for directing a gas (e.g., air) onto stent 10 to induce or inhibit evaporation of the solvent from the composition applied on stent 10. In one embodiment, blower 46 can include a heating device (not shown) so that blower 46 can deliver warm gas for the removal of the solvent. The heating device can be any heating device as known by those of ordinary skill in the art. For example, the heating device can be an electric heater incorporating heating coils. In a further embodiment, blower 46 can include a cooling device (not shown) so that blower 46 can deliver cool gas to inhibit evaporation of the solvent. The cooling device can be any cooling device as known by those of ordinary skill in the art. For example, the cooling device can be a thermoelectric cooling device incorporating a Peltier element.

Figure 3A:
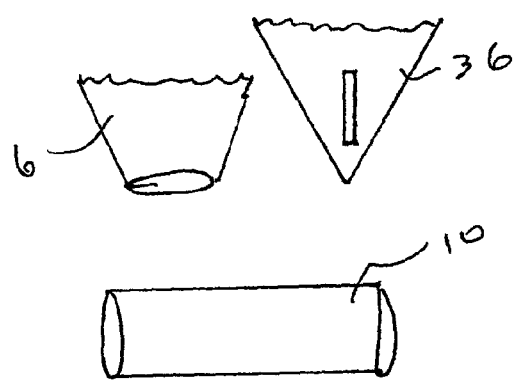
FIGS. 3A-3C illustrate various relative positions of a sprayer and a blower.
Figure 3B:
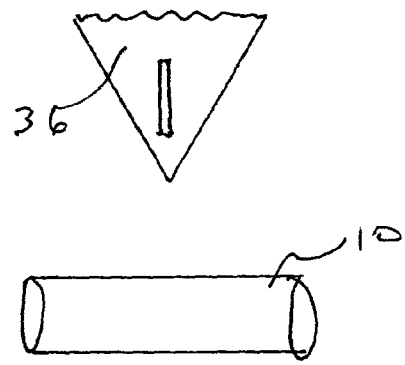
Figure 3C:
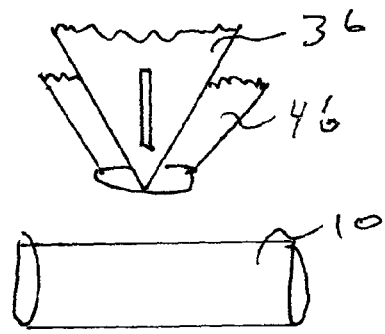

Blower 46 can be oriented at any angle relative to the longitudinal axis of stent 10. For example, as shown in FIG. 2, blower 46 can be oriented at about a 45° angle relative to the longitudinal axis of stent 10. In one embodiment, blower 46 can be oriented at the same angle as sprayer 36 so that the stream of gas directed by blower 46 is at the same angle (e.g., 90° relative to the longitudinal axis of stent 10) as the spray pattern from nozzle 40. Also, blower 46 can be at any position relative to sprayer 36. For instance, as shown in FIGS. 3A-3C, blower 46 can be adjacent to (FIG. 3A), opposite of (FIG. 3B) or behind (FIG. 3C) sprayer 36.

Any suitable gas can be delivered by blower 46, examples of which include air, argon or nitrogen. In an embodiment of the present invention, the system can include an air chamber 48 in communication with blower 46 via conduit 50. Air chamber 48 can store pressurized gas such as nitrogen that can be delivered by blower 46.

A controller 52 (e.g., a CPU) can be used to control the operation of the system. For instance, controller 52 can send signals to air pump 30 and blower 46 in order to control the operations of air pump 30 and blower 46. More particularly, controller 52 can control the temperature and the flow speed of the gas delivered by blower 46. Controller 52 can also send signals to sprayer 36, atomizing gas source 42 and actuating gas source 44 in order to control the application of the solution. For instance, controller 52 can synchronize the operations of air pump 30 and/or sprayer 36 and blower 46 so that blower 46 can direct a gas onto stent 10 simultaneous with the application of the solution by sprayer 36.

The system for coating a stent can also include a support structure for stent 10 such as a mandrel 54 attached to a first motor 56. Mandrel 54 and first motor 56 can rotate stent 10 about the device's central longitudinal axis. In addition, a second motor 58 can be movably disposed on a rail 60 so that second motor 58 can move stent 10 and mandrel 54 in a linear direction along the longitudinal axis of stent 10.

The system can further include a pressure gauge (not shown) that is capable of monitoring the back pressure of the solution flowing through nozzle 40. The reading of the pressure gauge can be compared with the pressure delivered by air pump 30 to determine if nozzle 40 is becoming clogged during the application process. If such clogging occurs, controller 52 can compensate for the pressure differential by adjusting the activity of air pump 30 and/or sprayer 36.

Also, the system can include a collection funnel 62 that collects the excess solution that does not remain on stent 10 during the spraying process. Collection funnel 62 may include vacuum means to collect more of the atomized solution.

Coating A Stent

During the application of the composition, the stent can be rotated about the stent's central longitudinal axis. Rotation of the stent can be from about 0.1 rpm to about 300 rpm, more narrowly from about 30 rpm to about 200 rpm. By way of example, the stent can rotate at about 150 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle).

The atomization pressure can be maintained at a range of about 5 psi to about 30 psi. The droplet size depends on factors such as viscosity of the solution, surface tension of the solvent, and atomization pressure. The flow rate of the composition from the spray nozzle can be from about 0.01 mg/second to about 1.0 mg/second, for example about 0.1 mg/second. Only a small percentage of the composition that is delivered from the spray nozzle is ultimately deposited on the stent. By way of example, when a composition is sprayed to deliver about 1 mg of solids, only about 100 micrograms or about 10% of the solids sprayed will likely be deposited on the stent.

The composition can be applied in multiple repetitions, wherein each repetition can be, for example, about 0.5 second to about 20 seconds, for example about 10 seconds in duration. The amount of coating applied by each repetition can be about 1 microgram/cm$^2$ (of stent surface) to about 50 micrograms/cm$^2$, for example less than about 20 micrograms/cm$^2$ per 1-second spray.

Each repetition can be followed by an application of a gas. The gas can be directed onto the stent following a waiting period of about 0.1 second to about 5 seconds after the application of the coating composition so as to allow the liquid sufficient time to flow and spread over the stent surface before the solvent(s) is removed to form a coating. The waiting period is particularly suitable if the coating composition contains a volatile solvent since such solvents are typically removed quickly. As used herein "volatile solvent" means a solvent that has a vapor pressure greater than 17.54 Torr at ambient temperature, and "non-volatile solvent" means a solvent that has a vapor pressure less than or equal to 17.54 Torr at ambient temperature.

Any suitable gas can be employed, examples of which include air, argon or nitrogen. The flow speed of the gas directed onto the stent can be from about 300 feet/minute (91.5 meters/minute) to about 10,000 feet/minute (3047.85 meters/minute), more narrowly about 2500 feet/minute (761.96 meters/minute) to about 6000 feet/minute (1828.71 meters/minute). After each repetition, the gas can be applied for about 1 second to about 100 seconds, more narrowly for about 2 seconds to about 20 seconds.

Evaporation of the solvent(s) can be induced by an application of a warm gas between each repetition which can prevent coating defects and minimizes interaction between the active agent and the solvent. A warm gas may be particularly suitable for embodiments in which the solvent employed in the coating composition is a non-volatile solvent (e.g., dimethylsulfoxide (DMSO), dimethylformamide (DMF), and dimethylacetamide (DMAC)). The temperature of the warm gas can be from about 25° C. to about 200° C., more narrowly from about 40° C. to about 90° C. By way of example, warm gas applications can be performed at a temperature of about 60° C., at a flow speed of about 5,000 feet/minute, and for about 10 seconds.

Any suitable number of repetitions of applying the composition followed by removing the solvent(s) can be performed to form a coating of a desired thickness or weight. Excessive application of the polymer can, however, cause coating defects. In embodiments in which the coating composition contains a volatile solvent, a waiting period of from about 0.1 second to about 20 seconds can be employed between solvent removal of one repetition and composition application of the subsequent repetition so as to ensure that the coating composition wets the surface before the accelerated removal of the solvent by the applied gas, thereby promoting coating uniformity.

In an embodiment of the present invention, a gas can be directed onto the stent to inhibit evaporation of the solvent from the composition. Inhibition of evaporation of a solvent may be useful if the solvent is extremely volatile because the solvent may evaporate too quickly leaving a rough coating surface on the stent. In one embodiment, in order to reduce the rate of evaporation of a solvent(s), a cool gas with a temperature of about less than 25° C. can be directed onto the stent after each repetition to inhibit the solvent's evaporation. The temperature of the gas can be, for example, significantly less than the boiling temperature of the solvent.

In an embodiment, a gas can be directed onto the stent simultaneously with the application of the composition in order to either induce evaporation or to inhibit evaporation. If a gas is directed onto the stent simultaneous with the application of the composition, the coating may be applied without interruption. If the gas is applied to facilitate faster removal of the solvent, the gas may decrease the total application time needed to coat an implantable device. Also, the application of a gas simultaneous with the application of the composition prevents coating defects and may minimize interaction between the active agent and the solvent. However, if the flow speed of the gas is too high, the direction of the composition spray may be affected by the gas as the composition is being applied to the stent. In some cases, it may be necessary to reposition the sprayer, the blower and the stent relative to each other in order to ensure that the composition spray is directed onto the stent.

Furthermore, the stent can be warmed to a temperature of from about 35° C. to about 80° C. prior to the application of the coating composition so as to facilitate faster removal of the solvent(s). In addition, the stent can be cooled prior to the application of the coating composition so as to inhibit evaporation of the solvent(s). The particular temperature selected depends, at least in part, on the particular solvent(s) used and the active agent employed in the coating composition. By way of example, pre-heating of the stent prior to applying a composition containing actinomycin D should be performed at a temperature not greater than about 55° C. Pre-heating is particularly suitable for embodiments in which the solvent(s) employed in the coating composition has a high boiling point, i.e., a solvent having a boiling point of, for example, >130° C. at ambient pressure (e.g., dimethylsulfoxide (DMSO), dimethylformamide (DMF), and dimethylacetamide (DMAC)).

In addition, the temperature of the composition can be adjusted to a temperature other than ambient temperature. The temperature of the composition, for instance, can be adjusted contemporaneously with the spraying of the composition. For example, the temperature of the coating solution can be maintained between 25° C. to about 60° C. as the composition is being applied to the surface of the stent.

Operations such as wiping, centrifugation, or other web clearing acts can be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

The stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "web" formation between the stent struts.

A final heat treatment can be conducted to remove essentially all of the solvent(s) from the composition on the stent. The heat treatment can be conducted at about 30° C. to about 200° C. for about 15 minutes to about 16 hours, more narrowly at about 50° C. to about 100° C. for about 1 hour to about 4 hours. By way of example, the heat treatment can be conducted at about 75° C. for 1 hour. The temperature of exposure should not adversely affect the characteristics of the active agent or of the coating. The heating can be conducted in an anhydrous atmosphere and at ambient pressure. The heating can, alternatively, be conducted under a vacuum condition. It is understood that essentially all of the solvent(s) will be removed from the composition but traces or residues can remain blended in the coating.

The particular thickness of the coating is based on the type of procedure for which the stent is employed and the amount, if any, of therapeutic substances or active agents that are desired to be delivered. By way of example and not limitation, the coating can have a thickness of about 0.05 microns to about 10 microns. Applying a plurality of reservoir coating layers, containing the same or different active agents, onto the stent can further increase the amount of the active ingredient to be carried by the stent, without causing coating defects.

Embodiments of the Composition

In accordance with one embodiment, the composition can include a solvent and a polymer dissolved in the solvent. The composition can also include active agents, radiopaque elements, or radioactive isotopes. Representative examples of polymers that can be used to coat an implantable device in accordance with the present invention include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-covalerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; rayon; rayon-triacetate; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Representative examples of solvents include chloroform, acetone, water (buffered saline), dimethylsulfoxide (DMSO), propylene glycol methyl ether (PM) iso-propylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the active agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. TAXOTERE®, from Aventis S.A., Frankfurt, Germany) methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX® (bivalirudin, Biogen, Inc., Cambridge, Mass.). Examples of such cytostatic or antiproliferative agents include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINVIL® and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. The foregoing substances are listed by way of example and are not meant to be limiting. Other active agents which are currently available or that may be developed in the future are equally applicable.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

Optional Coating Layers

In one embodiment, an optional primer layer can be formed prior to the reservoir coating to increase the retention of the reservoir coating on the surface of the stent, particularly metallic surfaces such as stainless steel. The primer layer can act as an intermediary adhesive tie layer between the surface of the device and a reservoir coating carrying an active agent, allowing for the quantity of the active agent to be increased in the reservoir coating.

To form an optional primer layer on the surface of the stent, a composition that is free from active agents is applied to the surface of the stent. Application of the composition and evaporation of the solvent to form the primer layer can be accomplished via embodiments of the above-described system and method of the present invention. Ethylene vinyl alcohol copolymer, for example, adheres very well to metallic surfaces, particularly stainless steel. Accordingly, the copolymer provides for a strong adhesive tie between the reservoir coating and the surface of the implantable device. With the use of thermoplastic polymers such as, but not limited to, ethylene vinyl alcohol copolymer, polycaprolactone, poly (lactide-co-glycolide), and poly(hydroxybutyrate), the deposited primer composition should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of the implantable device. The prosthesis should be exposed to the heat treatment for any suitable duration of time that will allow for the formation of the primer layer on the surface of the implantable device and for the evaporation of the solvent employed. By way of example and not limitation, the optional primer layer can have a thickness of about 0.01 microns to about 2 microns. The application of the reservoir coating should be performed subsequent to the drying of the optional primer layer.

In another embodiment, an optional diffusion barrier can be formed over a reservoir coating containing an active agent to reduce the rate at which the active agent is released from the coated stent. A composition, free from any active agents, can be applied to a selected portion of the reservoir coating subsequent to the drying of the reservoir coating. The diffusion barrier may be composed of a different polymer from that used in the reservoir coating or the same material. Application of the composition and evaporation of the solvent to form the diffusion barrier can be accomplished via the embodiments of the above-described system and method of the present invention. The diffusion barrier can have a thickness of about 0.2 microns to about 10 microns. It is understood by one of ordinary skill in the art that the thickness of the diffusion barrier is based on factors such as the type of stent, the type of procedure for which the stent is employed, and the rate of release that is desired. As described above with reference to the reservoir coating, a final heat treatment can be conducted to remove essentially all of the solvent(s) from the optional diffusion barrier.

Method of Use

In accordance with embodiments of the above-described method, an active agent can be applied to an implantable device or prosthesis, e.g., a stent, retained on the stent during delivery and expansion of the stent, and released at a desired rate and for a predetermined duration of time at the site of implantation. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Four 8 mm Multi-Link TETRA stents (available from Guidant Corporation) were cleaned by sonication in water, followed by sonication in isopropanol. The stents were dried at 70° C. and plasma cleaned in an argon plasma chamber.

Each unexpanded stent was positioned on a mandrel such that the mandrel contacted the stent at its opposing ends. An EFD 780S spray device with VALVEMATE 7040 control system (manufactured by EFD Inc., East Providence, R.I.) was used to apply the coating compositions to the stents. The spray nozzle was adjusted to provide a distance from the nozzle tip to the outer surface of the stent of approximately 4.5 cm and a spray angle of approximately 90° relative to the horizontal stents. The atomization pressure was set to be maintained throughout the coating process at 20 psi.

Each stent was passed under the spray nozzle for about 2 seconds. A composition containing 2% (w/w) poly-n-butyl methacrylate (PBMA) 337K molecular weight in cyclohexanone:ethyl acetate (1:1) (w/w) was sprayed onto one stent. A composition containing 2% (w/w) PBMA 649K in cyclohexanone:ethyl acetate (1:1) was sprayed onto two stents. A composition containing 2% (w/w) PBMA 857K molecular weight in cyclohexanone:ethyl acetate (1:1) was sprayed onto one stent. Each stent was rotated about the stent's central longitudinal axis at a speed of 3 rpm during coating. After a waiting period of 1 second following the application of the respective compositions, warm air of approximately 80° C. was directed from an air gun onto each stent for 15 seconds to remove most of the solvents. The spraying-blowing cycle was repeated to deposit thirty-four layers on each stent, with a wait time of 5 seconds between each cycle. The coated stent was allowed to dry for about 60 minutes under vacuum conditions in an oven at a temperature of about 70° C.

Each of the four coated stents had a uniform, smooth coating. In addition, the stent sprayed with 2% (w/w) PBMA 857K molecular weight in cyclohexanone:ethyl acetate (1:1) was submitted for a simulated use test and was found to have good mechanical properties, no cracking, and good coating adhesion.

Example 2

An 8 mm Multi-Link TETRA stent was cleaned by placement in an ultrasonic bath of isopropyl alcohol solution for 15 minutes. The stent was dried and plasma cleaned in a plasma chamber.

A composition containing 2% (w/w) poly-n-butyl methacrylate (PBMA) and 2% (w/w) quinoline yellow dye in chloroform:cyclohexanone (9:1) was prepared.

The unexpanded stent was positioned on a mandrel such that the mandrel contacted the stent at its opposing ends. An EFD 780S spray device with VALVEMATE 7040 control system was used to apply the coating composition to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi.

The stent was passed under the spray nozzle for about 1 second. The stent was rotated about the stent's central longitudinal axis at a speed of 3 rpm during coating. Warm air of approximately 100° C. was directed from an air gun onto the stent for 4 seconds to remove most of the solvents. The spraying-heating cycle was repeated to deposit forty layers on the stent, depositing about 300 micrograms of coating. The coated stent was allowed to dry for about 3 hours under vacuum conditions at a temperature of about 75° C. The coated stent had a uniform, smooth coating with an estimated dye content of about 130 micrograms or 43% of the total amount of coating deposited.

Example 3

An 8 mm Multi-Link TETRA stent was cleaned by placement in an ultrasonic bath of isopropyl alcohol solution for 15 minutes. The stent was dried and plasma cleaned in a plasma chamber.

A primer composition containing 2% (w/w) poly-n-butyl methacrylate (PBMA) was prepared. A reservoir composition containing 2% (w/w) PBMA and 2.7% (w/w) ethyl eosin dye in methanol:cyclohexanone (1:1) was also prepared. In addition, a diffusion barrier composition containing 2% (w/w) PBMA was prepared.

The unexpanded stent was positioned on a mandrel such that the mandrel contacted the stent at its opposing ends. An EFD 780S spray device with VALVEMATE 7040 control system was used to apply the various compositions to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi. The stent was rotated about the stent's central longitudinal axis at a speed of 3 rpm during coating.

The primer composition was applied to the stent by passing the stent under the spray nozzle for about 0.75 second. Warm air of approximately 100° C. was directed from an air gun onto the stent for 8 seconds to remove most of the solvents and form a primer layer on the stent. The reservoir composition was then applied to the primered stent by passing the stent under the spray nozzle for about 0.75 second. Warm air of approximately 100° C. was directed from an air gun onto the stent for 4 seconds to remove most of the solvents. The spraying-heating cycle was repeated to deposit forty layers on the stent, depositing about 419 micrograms of the reservoir coating. The coated stent was allowed to dry for about 3 hours under vacuum conditions at a temperature of about 75° C. The barrier layer composition was then applied to the reservoir-coated stent by passing the stent under the spray nozzle for about 0.75 second. Warm air of approximately 100° C. was directed from an air gun onto the stent for 4 seconds to remove most of the solvents. The spraying-heating cycle was repeated to deposit about 70 micrograms of the diffusion barrier. The coated stent was allowed to dry overnight under vacuum conditions at a temperature of about 75° C. The coated stent had a uniform, smooth coating with an estimated dye content of about 224 micrograms or 53% of the total amount of coating deposited.

Example 4

An 8 mm Multi-Link TETRA stent was cleaned by placement in an ultrasonic bath of isopropyl alcohol solution for 15 minutes. The stent was dried and plasma cleaned in a plasma chamber.

A composition containing 2% (w/w) poly-n-butyl methacrylate (PBMA) and 2% (w/w) quinoline yellow dye in chloroform:cyclohexanone (9:1) was prepared.

The unexpanded stent was positioned on a mandrel such that the mandrel contacted the stent at its opposing ends. An EFD 780S spray device with VALVEMATE 7040 control system was used to apply the composition to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi.

The stent was passed under the spray nozzle for about 1.5 second. The stent was rotated about the stent's central longitudinal axis at a speed of 3 rpm during coating. Warm air of approximately 100° C. was directed from an air gun onto the stent for 4 seconds to remove most of the solvents. The spraying-heating cycle was repeated to deposit 3 layers on the stent, depositing about 115 micrograms of coating. The coated stent was allowed to dry for about 3 hours under vacuum conditions at a temperature of about 75° C. The coated stent had a uniform, smooth coating with an estimated dye content of about 38 micrograms or 33% of the total amount of coating deposited.

Example 5

To determine the maximum amount of coating that could be deposited on an 8 mm stent without visible webbing, a Multi-Link TETRA stent was coated using the same coating composition and parameters as described in Example 4. The spraying-heating cycle was repeated until 790 micrograms of coating had been deposited on the stent, at which time no webbing was observed.

Example 6

An 8 mm Multi-Link TETRA stent was cleaned by placement in an ultrasonic bath of isopropyl alcohol solution for 15 minutes. The stent was dried and plasma cleaned in a plasma chamber.

A composition containing 2% (w/w) poly-n-butyl methacrylate (PBMA) and 2% (w/w) solvent blue dye in chloroform:cyclohexanone (9:1) was prepared.

The unexpanded stent was positioned on a mandrel such that the mandrel contacted the stent at its opposing ends. An EFD 780S spray device with VALVEMATE 7040 control system was used to apply the composition to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi.

The stent was passed under the spray nozzle for about 1.5 seconds. The stent was rotated about the stent's central longitudinal axis at a speed of 3 rpm during coating. Warm air of approximately 100° C. was directed from an air gun onto the stent for 4 seconds to remove most of the solvents. The spraying-heating cycle was repeated to deposit about 130 micrograms of coating. The coated stent was allowed to dry for about 3 hours under vacuum conditions at a temperature of about 75° C. The coated stent had a uniform, smooth coating with an estimated dye content of about 85 micrograms or 66% of the total amount of coating deposited.

Example 7

In this example, the composition was sprayed onto stents simultaneous with directing a gas onto the stents from a blower. The following equipment and materials were used for this example:

1. 13 mm, reject TETRA Stents (Guidant Corporation, Santa Clara, Calif.);
2. Optical inspection microscope, Stereo Zoom 4 (Bausch & Lomb, Rochester, N.Y.);
3. EVAL polymer lot LOEV34-19 (EVAL Company of America, Lisle, Ill.);
4. Dimethylacetamide, EM Sciences Omnisolv (EM Sciences, Gibbstown, N.J.);
5. EFD 10 cc polyethylene barrel (EFD Inc., East Providence, R.I.);
6. 10 cc Norm-Ject syringe (Air-Tite Products Co., Inc., Virginia Beach, Va.);
7. EFD Spray Nozzle 780S-33 with 7857F-46SS air cap and 7857-46SS nozzle (EFD Inc., East Providence, R.I.);
8. EFD 7040 Controller (EFD Inc., East Providence, R.I.);
9. Blower (Conair Corporation, East Windsor, N.J.);
10. Digital Thermometer #61220-416 (VWR International, West Chester, Pa.);
11. GT-21 Electric rotator (G.K. Heller Corp., Floral Park, N.Y.);
12. 0.45 mm Gelman nylon syringe filter (VWR International, West Chester, Pa.);
13. Stent coating mandrel with Teflon collets (constructed in-house at Guidant Corporation, Santa Clara, Calif.);
14. Baxter DN-43 Convection oven (VWR International, West Chester, Pa.); and
15. Mettler microbalance model UMT2 (Mettler-Toledo GmbH, Greifensee, Switzerland).

Stents were pre-expanded using a 0.071 bulbous mandrel, TLT 2011737-02 (constructed in-house at Guidant Corporation, Santa Clara, Calif.). They were then weighed and placed into new glass, 2 ml HPLC vials. No cleaning steps were undertaken. The coating solution was formulated at 2% (w/w) EVAL in DMAC by blending 1.33 g of a 15% (w/w) EVAL/DMAC solution with 8.67 g of DMAC.

In order to compare the importance of certain parameters, some parameters were varied while others remained constant. The variable parameters were (1) spray flow rate, (2) spray atomization pressure, (3) blower temperature, and (4) blower-stent distance. The parameters kept constant were (1) nozzle-stent distance (28 mm), (2) barrel pressure (2 psi), (3) stent rotation speed (120 rpm), and (4) blower-spray nozzle angle (about 40-45°).

Table I summarizes the experimental parameters.

TABLE I

| Stent # | Spray Flow Rate | Blower Temp. (° C.) | Spray Atomization Pressure (psi) | Blower-Stent Distance (cm) |
|---|---|---|---|---|
| 1 | Low | Ambient | 10 | 4 |
| 2 | Low | 64 | 30 | 4 |
| 3 | Low | Ambient | 30 | 4 |
| 4 | Low | 54 | 30 | 8 |
| 5 | Low | Ambient | 30 | 8 |
| 6 | High | 64 | 30 | 4 |
| 7 | High | Ambient | 30 | 4 |
| 8 | High | Ambient | 30 | 8 |
| 9 | High | 54 | 30 | 8 |

The determination of what was a low or a high spray flow rate was somewhat subjective. It was arrived at by spraying a glass slide and observing the amount of coating accumulating on the slide and comparing the results with what is typically seen when coating stents with similar methods.

Setting the blower at a blower-stent distance of about 4 cm with the heating element activated resulted in a temperature at that distance of about 64° C. At double the distance, 8 cm, the temperature was about 54° C. The temperature was measured by placing a digital thermometer at the stent position with the blower running continuously. By deactivating the heating element, the blower supplied air at ambient temperature.

The atomization pressures of 10 psi and 30 psi were selected as they represent the extremes that might be used. With some conventional methods, the atomization pressure is about 10-15 psi.

The EFD 7040 controller can spray for a maximum of 99.99 seconds. For each stent, it was first set to 30 seconds to determine an initial coating rate. After the stent rotator and the blower were turned on, the sprayer was run for 30 seconds. The stent was weighed and this weight uptake was used to calculate how much longer the stent needed to be sprayed to accumulate a total of approximately 300 μg of coating. The coating was then applied in continuous spray intervals of 90 seconds with the blower turned on. After coating, the stents were dried at 60° C. for 2 hours. A final weight was taken to get the dry coating weight. Scanning electron microscope (SEM) analysis was done on the stents using a Hitachi S-3000N (Hitachi Scientific Instruments, Pleasanton, Calif.). The stents were mounted on conductive carbon tape, gold sputtered, and imaged at 5 KeV.

Table II summarizes the coating results.

TABLE II

| Stent # | Stent Initial wt. (μg) | Gain after 30 sec Spray (μg) | Additional Spray Time (sec) | Wet wt. (μg) | Dried wt. (μg) | Final Gain (μg) |
|---|---|---|---|---|---|---|
| 1 | 19093 | 8 | 540 | 19358 | 19328 | 235 |
| 2 | 18299 | 19 | 450 | 18601 | 18576 | 277 |
| 3 | 18262 | 22 | 360 | 18523 | 18487 | 225 |
| 4 | 14736 | 17 | 540 | 15044 | 15014 | 278 |
| 5 | 15524 | 19 | 450 | 15807 | 15769 | 245 |
| 6 | 17617 | 35 | 235 | 17894 | 17868 | 251 |
| 7 | 19763 | 42 | 180 | — | 20046 | 283 |
| 8 | 17354 | 53 | 180 | — | 17617 | 263 |
| 9 | 18568 | 35 | 225 | 18863 | 18833 | 265 |

The wet weights of stents 7 and 8 were not taken. This is because a noticeable amount of coating fluid had built up on the teflon collet holding the distal end of the stent. It was felt that handling the stents could have moved this fluid onto other portions of the stents. Table III summarizes the process conditions, appearance of the stent, and coating rate.

TABLE III

| Stent # | Spray Flow Rate | Blower Temp. (° C.) | Spray Atomization Pressure (psi) | Blower-Stent Dist. (cm) | Gain After Drying (μg) | Total Coating Time (sec) | Coating Rate (μg/sec) | Coating Appearance by SEM |
|---|---|---|---|---|---|---|---|---|
| 1 | Low | ambient | 10 | 4 | 235 | 570 | 0.41 | Smooth, ridges |
| 2 | Low | 64 | 30 | 4 | 277 | 480 | 0.58 | Smooth |
| 3 | Low | ambient | 30 | 4 | 225 | 390 | 0.58 | Very smooth |
| 4 | Low | 54 | 30 | 8 | 278 | 570 | 0.49 | Smooth |
| 5 | Low | ambient | 30 | 8 | 245 | 480 | 0.51 | Very smooth |
| 6 | High | 64 | 30 | 4 | 251 | 265 | 0.95 | Smooth |
| 7 | High | ambient | 30 | 4 | 283 | 210 | 1.35 | Very smooth |
| 8 | High | ambient | 30 | 8 | 263 | 210 | 1.25 | Very smooth |
| 9 | High | 54 | 30 | 8 | 265 | 255 | 1.04 | Smooth |

Figure 4:
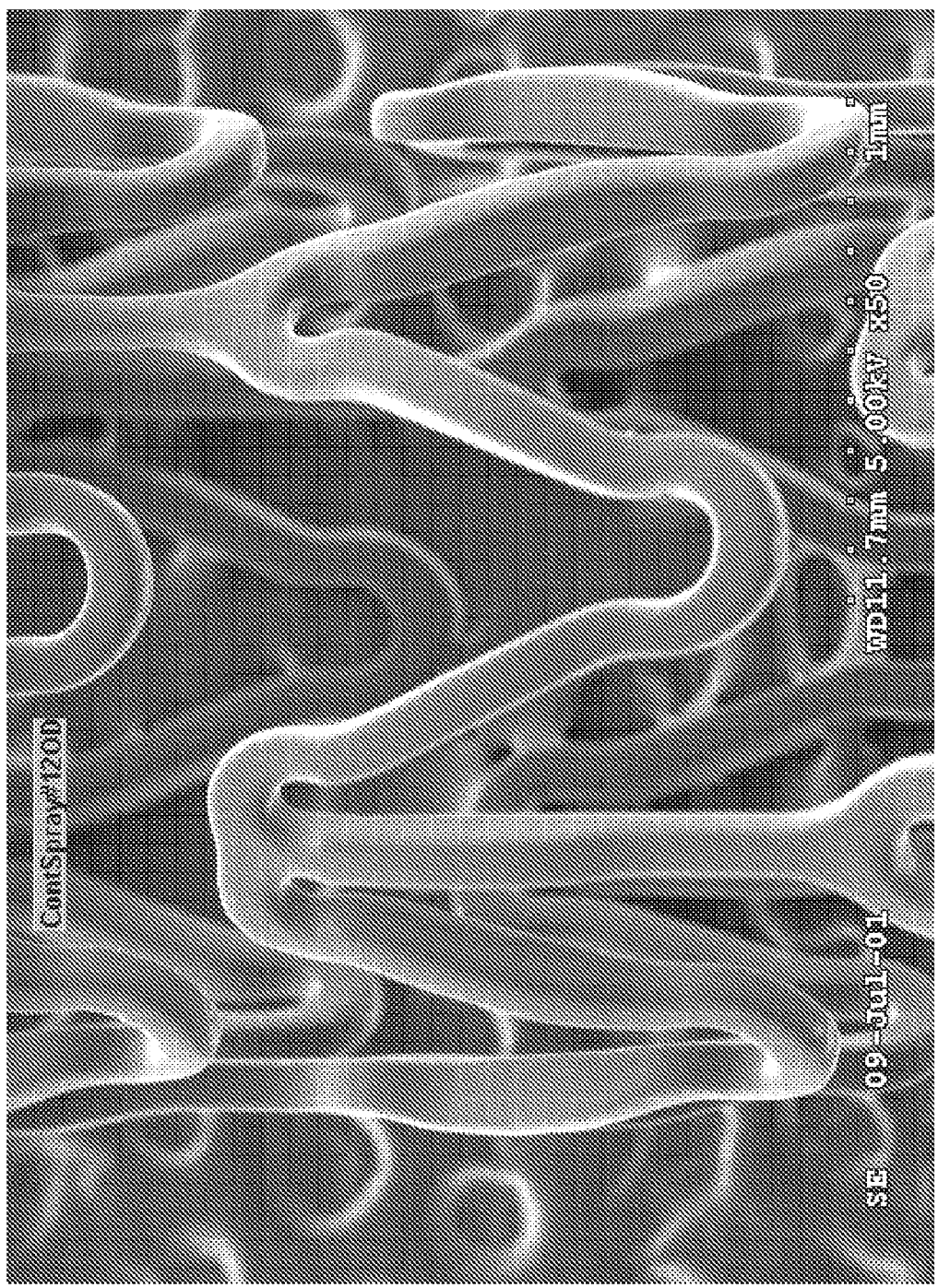
FIGS. 4-15 are scanning electron microscope images.
Figure 5:
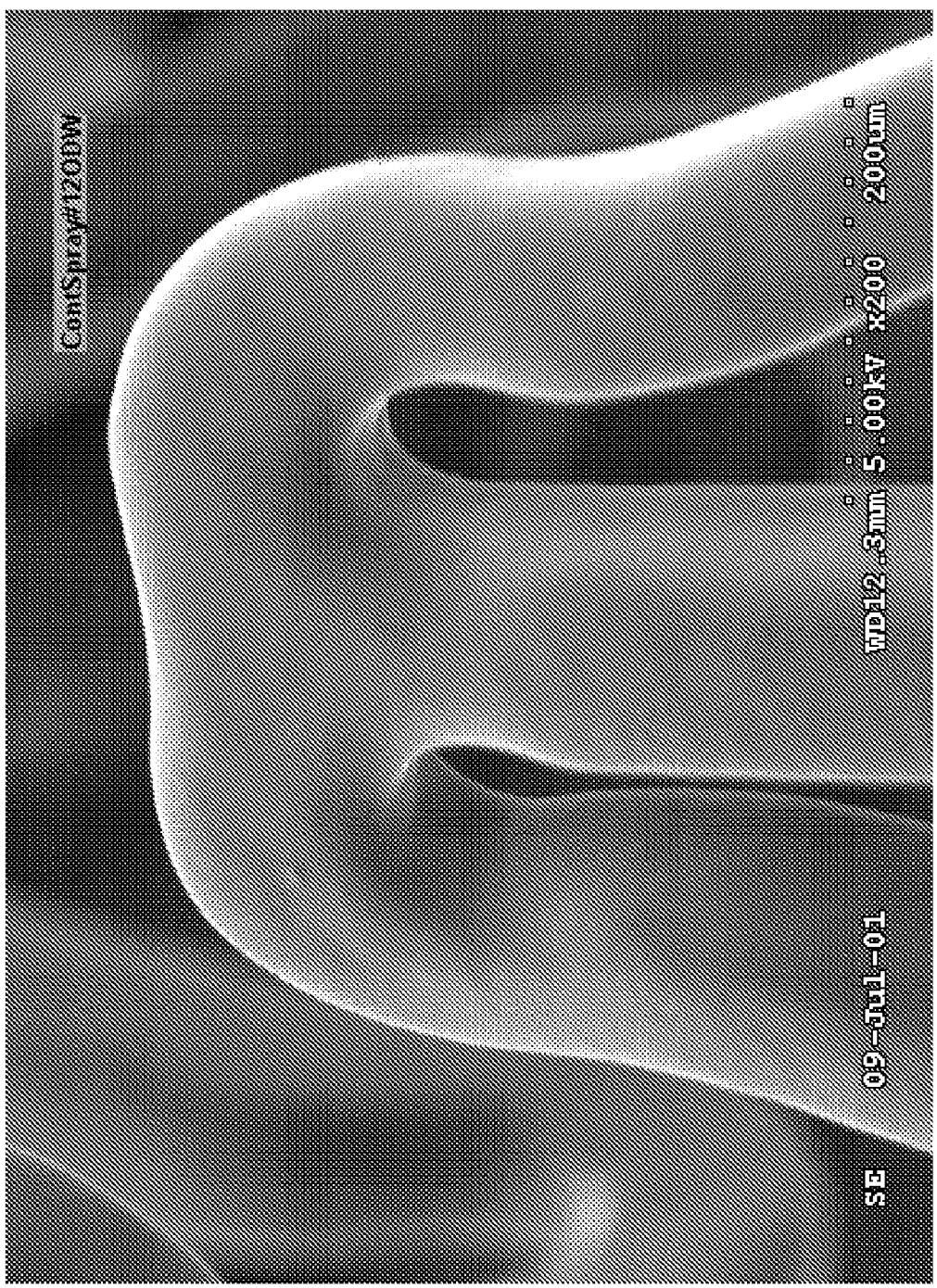
Figure 6:
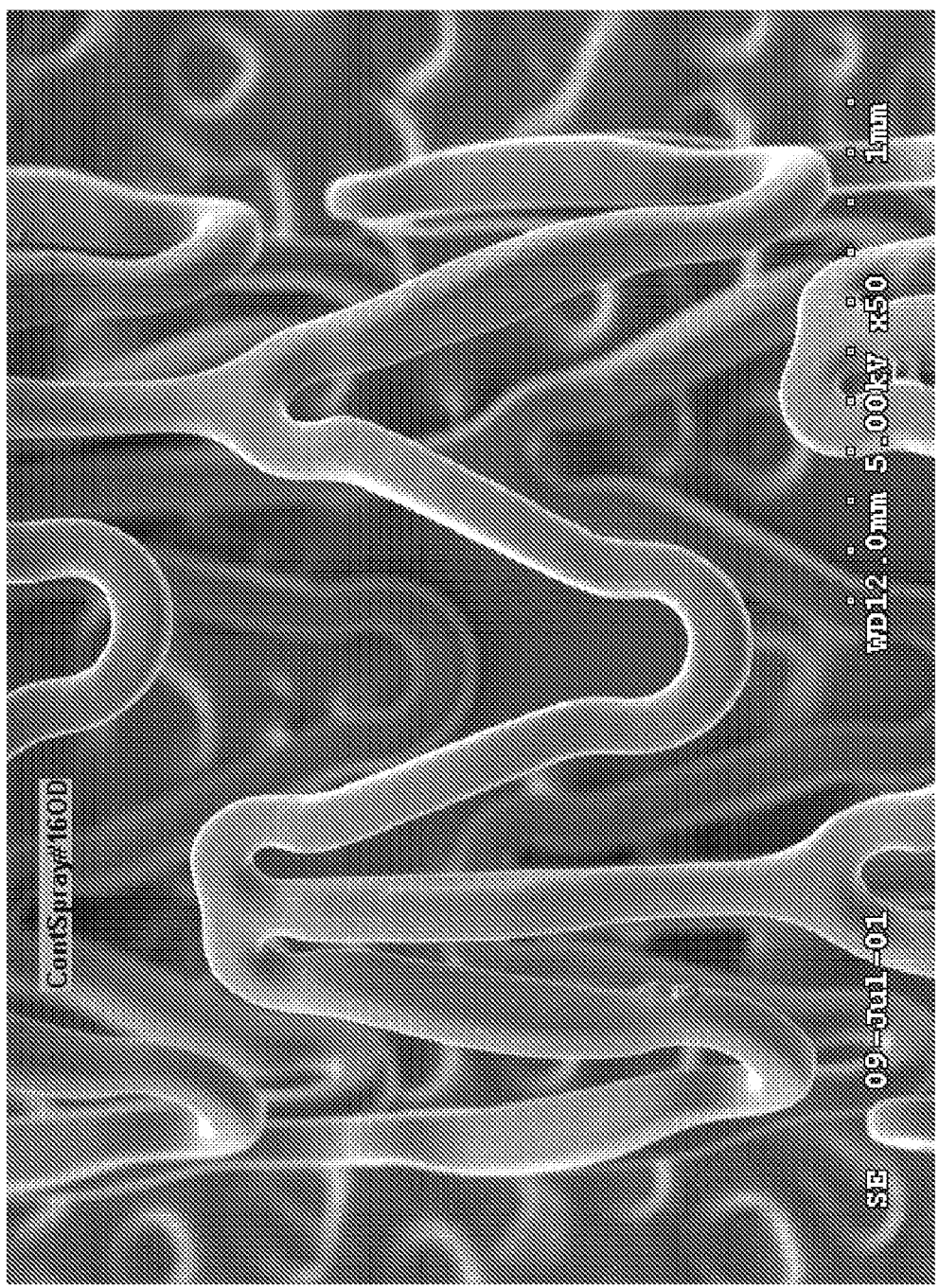
Figure 7:
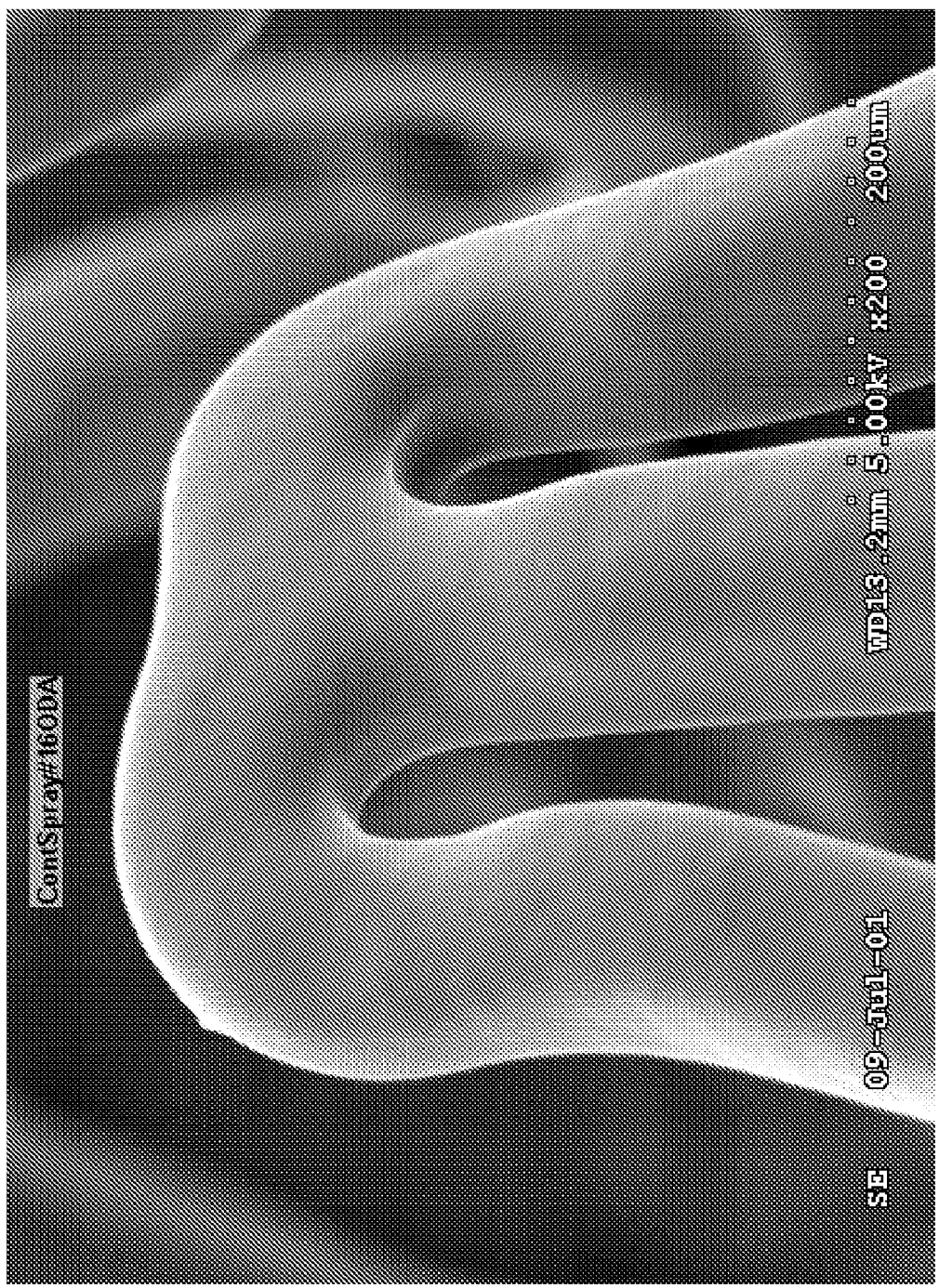

The coating rates for some of the stents produced by the process under this example were significantly high. For example, the coating rates for stents 7 and 8 were 1.35 μg/sec and 1.25 μg/sec, respectively. In addition to having fast coating rates, stents 7 and 8 had very smooth coating surfaces. The coating surface for stent 7 can be seen in FIGS. 4 and 5, and the coating surface for stent 8 can be seen in FIGS. 6 and 7. The composition was applied to stents 7 and 8 with a high spray flow rate, an ambient blower temperature, and a spray atomization pressure of about 30 psi. The only parameter that varied for stents 7 and 8 was the blower-stent distance.

Figure 8:
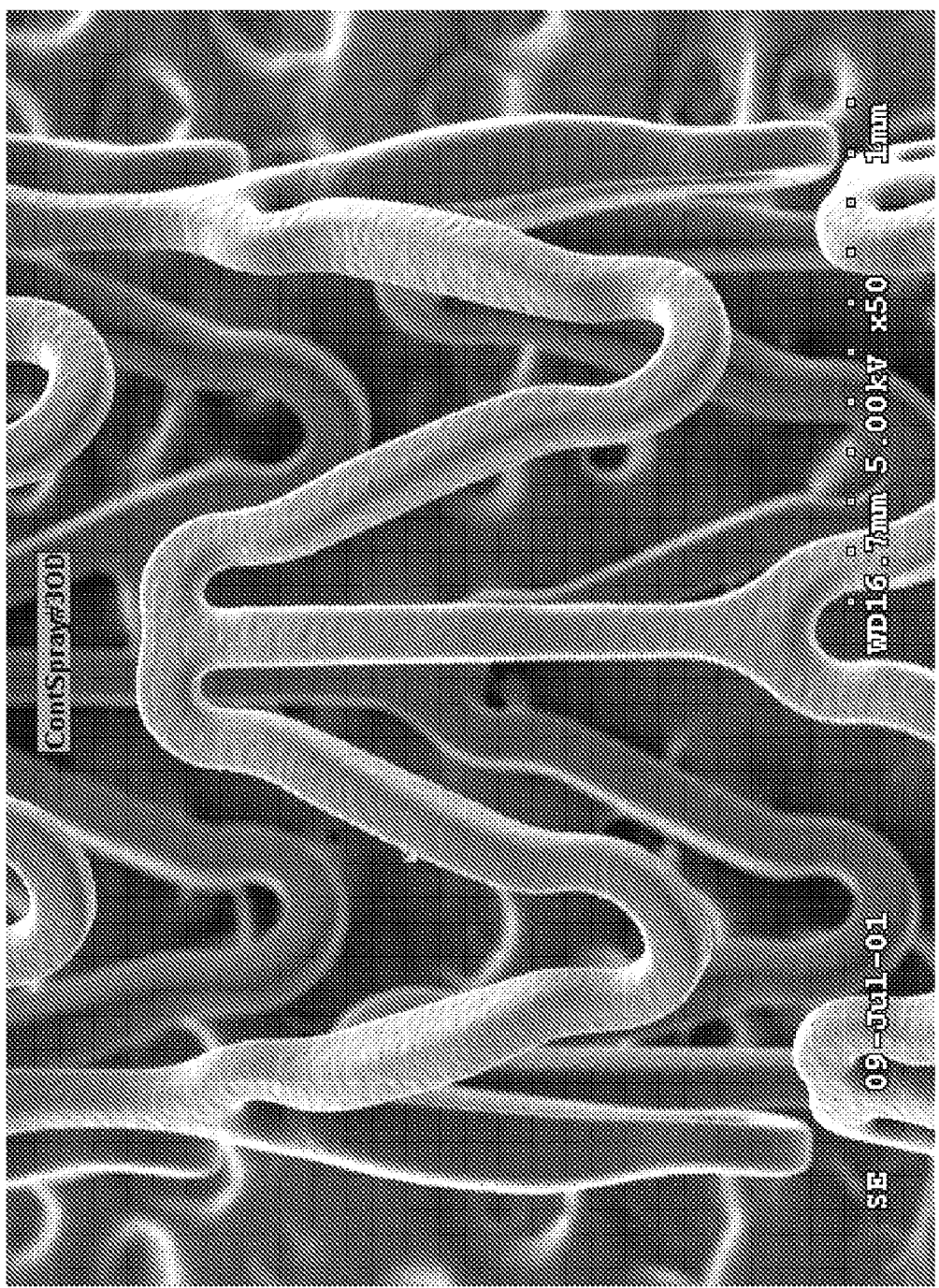
Figure 9:
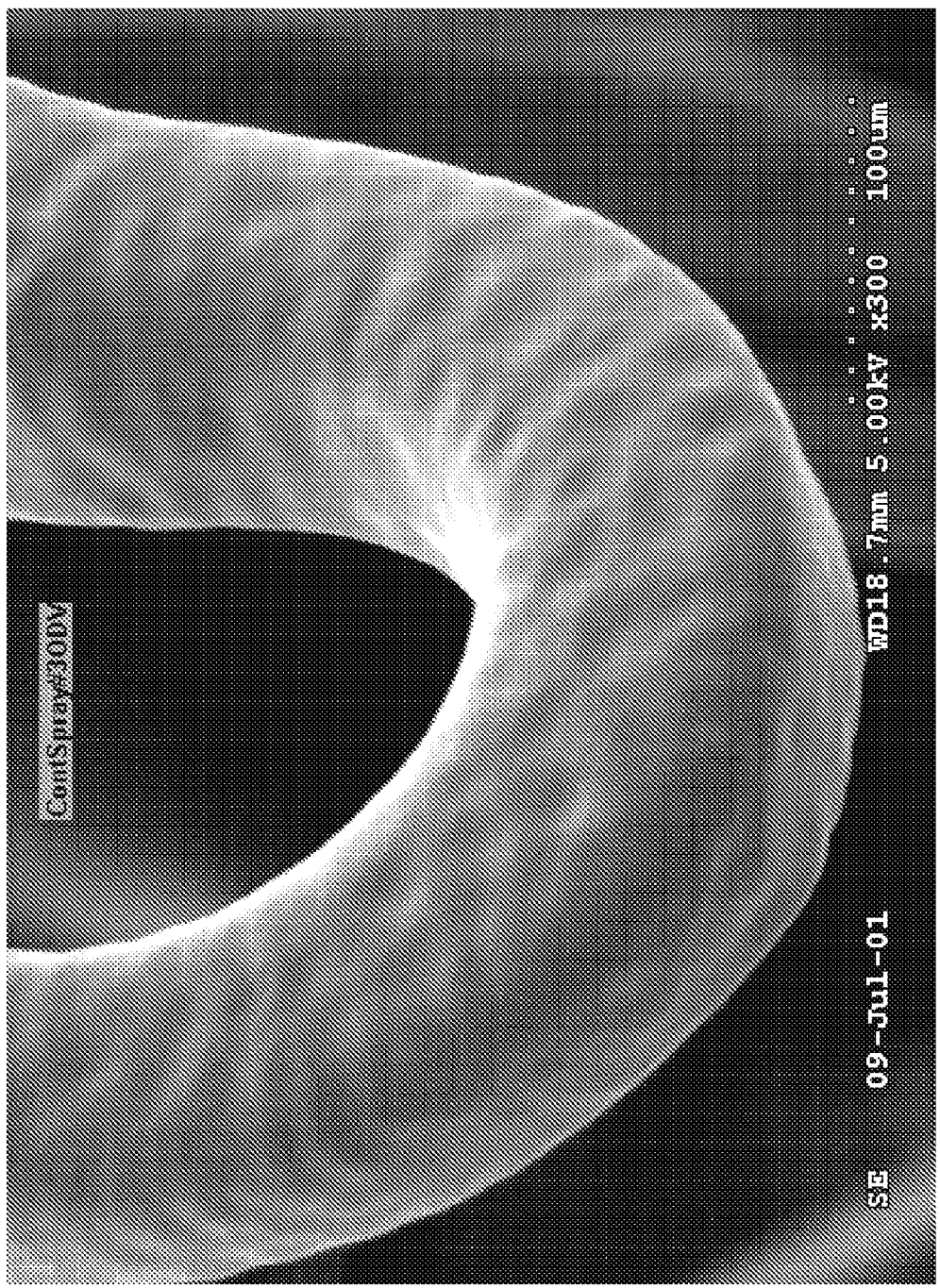
Figure 10:
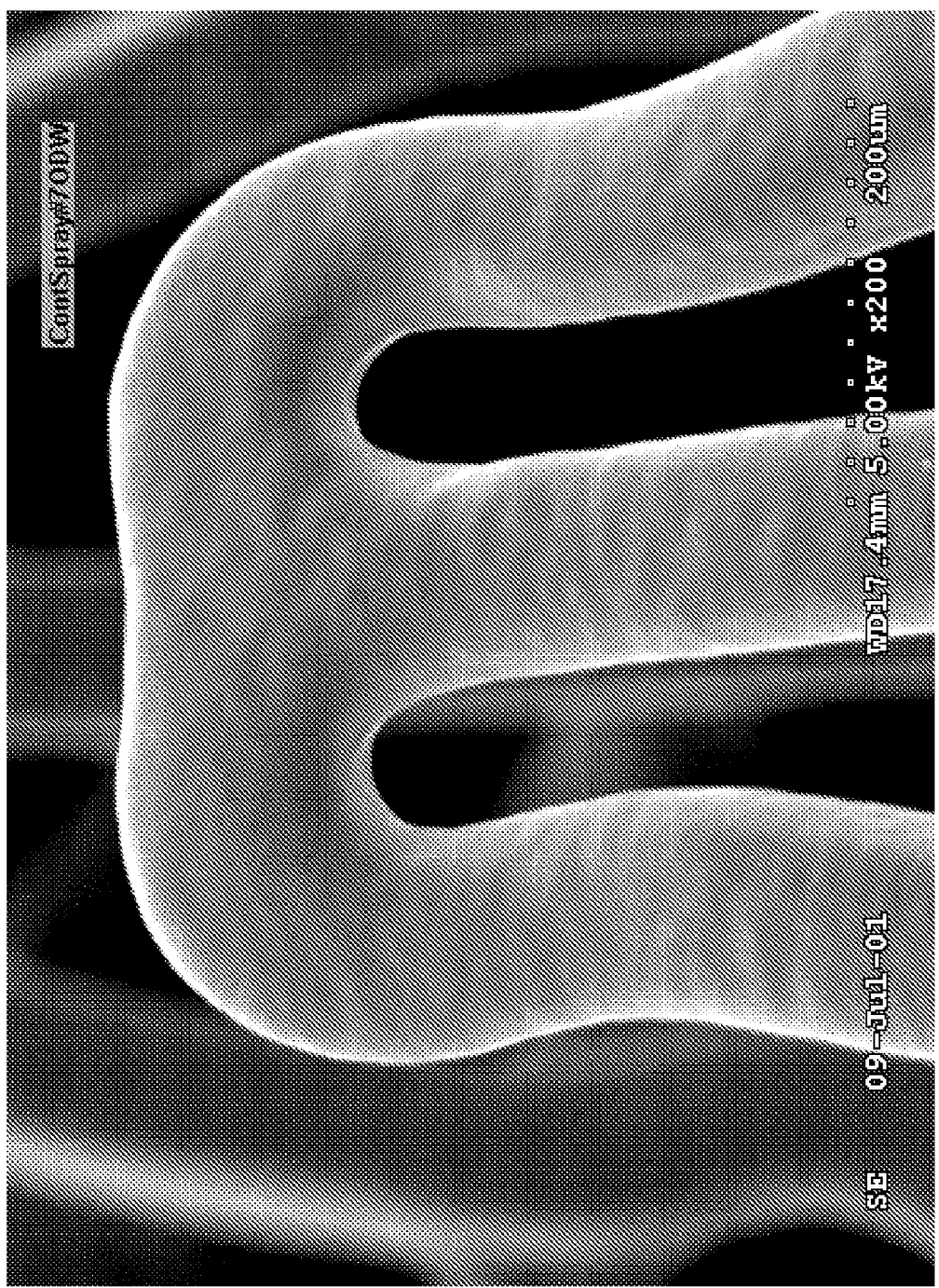
Figure 11:
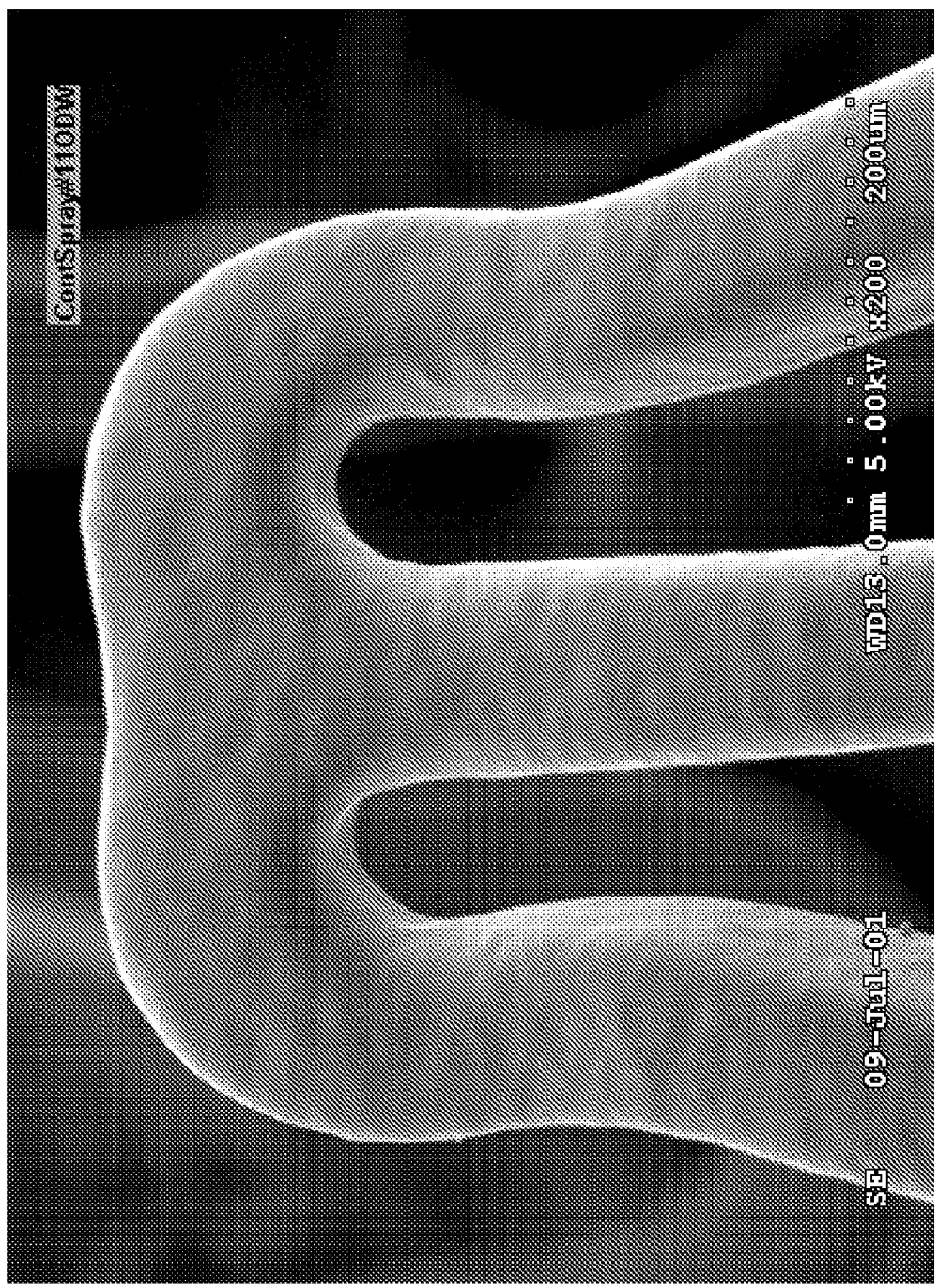
Figure 12:
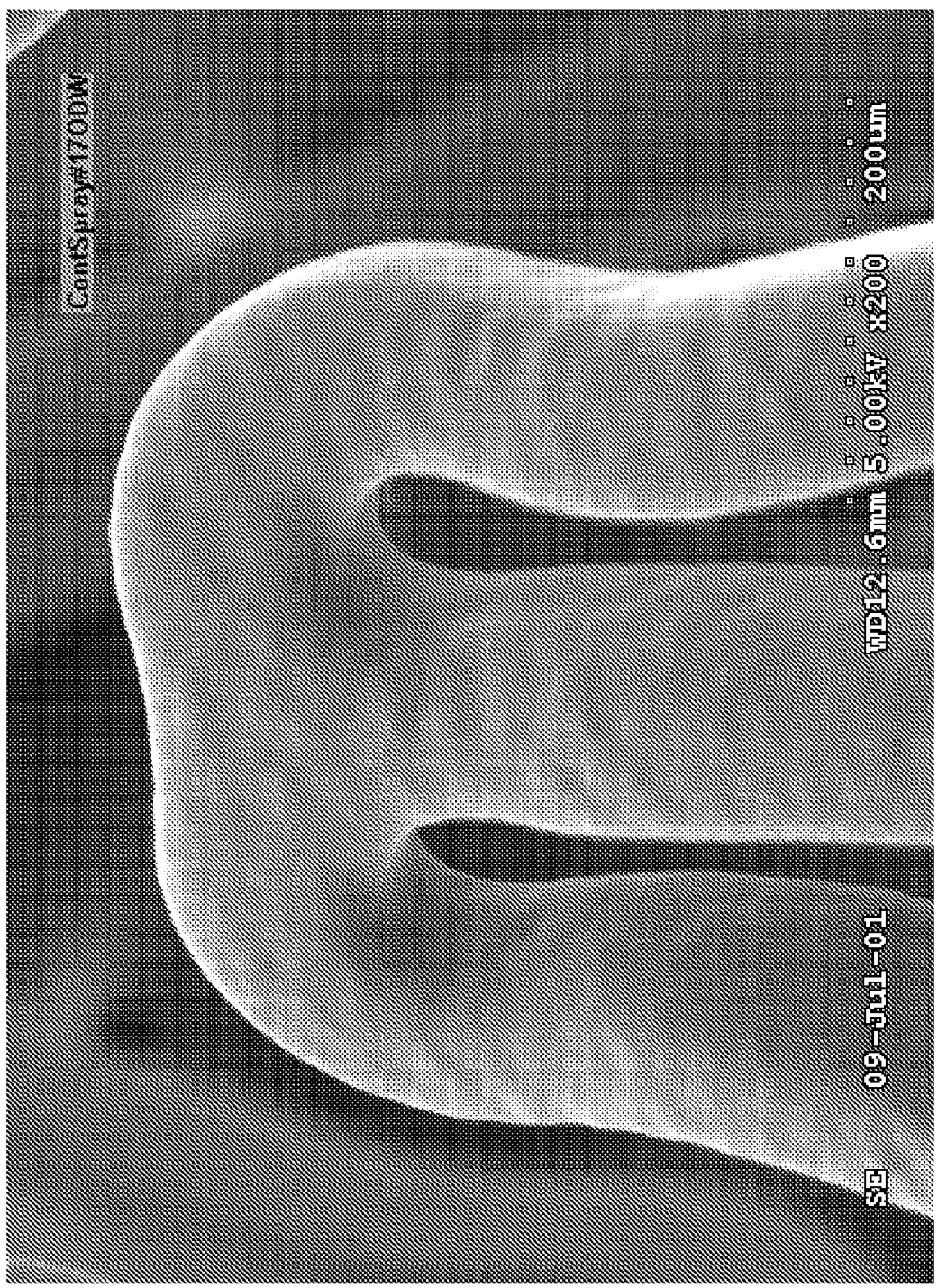

Besides stents 7 and 8, other stents had smooth coating surfaces. Referring to Table III, stents 2, 4, 6 and 9 had application conditions of a high blow temperature of about 54° C. or 64° C. and a high atomization pressure of about 30 psi. These shared parameters resulted in a smooth coating surface. For example, FIGS. 8 and 9 show a smooth coating surface for stent 2. The smooth coating surfaces of stents 4, 6, and 9, as shown in FIGS. 10, 11, and 12, respectively, are all similar to the coating surface of stent 2. Stents 4 and 6, however, may have slightly smoother coating surfaces than stent 2.

Figure 13:
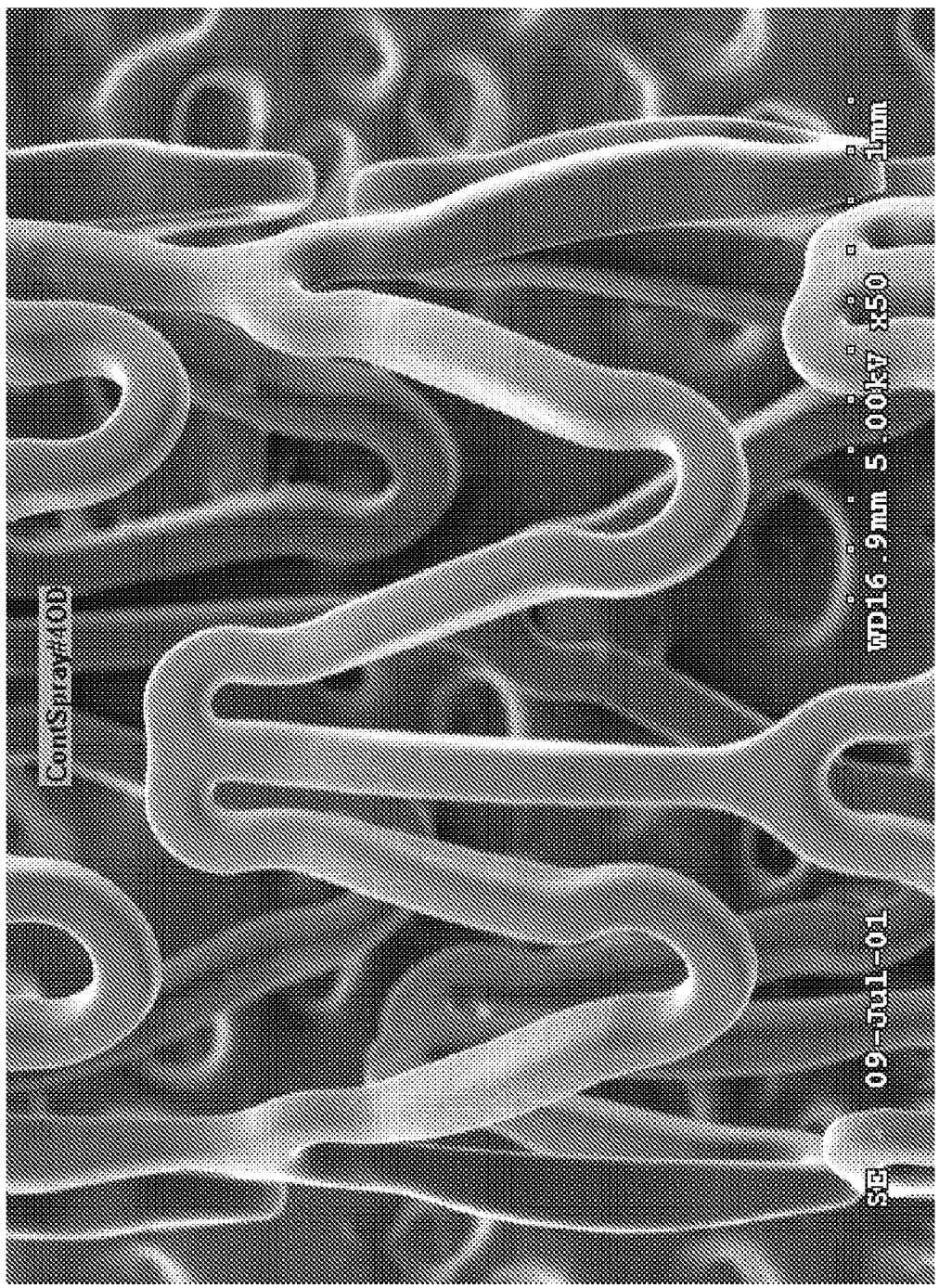
Figure 14:
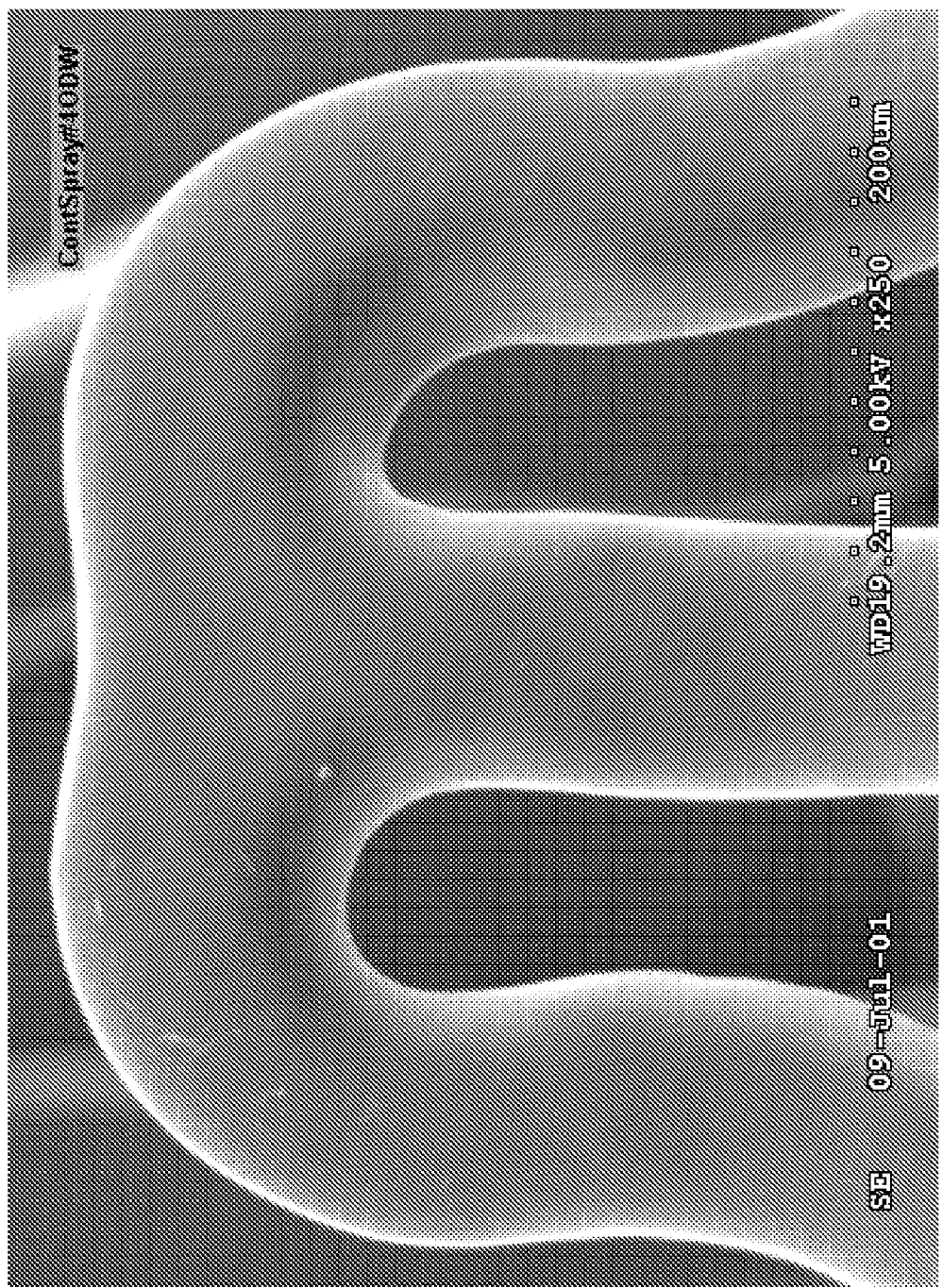
Figure 15:
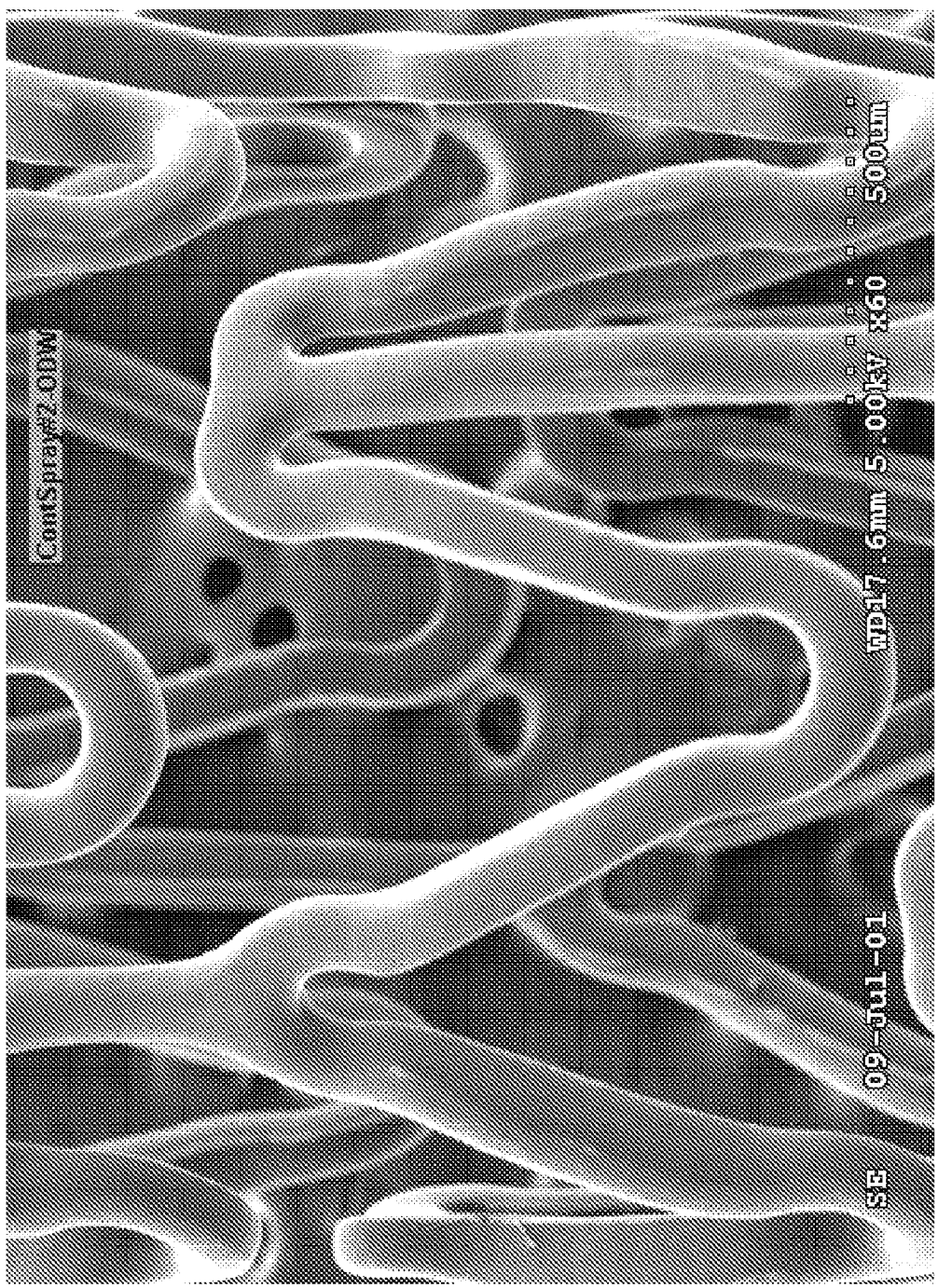

The composition was applied to stents 3, 5, 7 and 8 with an ambient blower temperature and a 30 psi atomization pressure. As shown in FIGS. 13 and 14, stent 3 had no noticeable webbing and a very smooth surface finish. Stents 5, 7, and 8 all had similar coating surfaces. Also, the composition was applied to stent 1 with parameters similar to those for stents 3, 5, 7, and 8, except that the atomization pressure was 10 psi. As shown in FIG. 15, the coating surface for stent 1 is smooth except for some ridges that may be seen on the strut edges.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating an implantable device comprising:
    applying a composition including a solvent to an implantable device; and
    actively directing a gas from a blowing means onto the implantable device, wherein if the solvent has a vapor pressure greater than 17.54 Torr at ambient temperature the temperature of the gas is adjusted to inhibit the evaporation of the solvent, and if the solvent has a vapor pressure of less than 17.54 Torr at ambient temperature the temperature of the gas is adjusted to induce the evaporation of the solvent.

2. The method of claim 1, wherein the implantable device is a radially expandable stent.

3. The method of claim 1, wherein the composition is applied simultaneous with the directing of the gas.

4. The method of claim 1, wherein the composition includes a polymer dissolved in the solvent and optionally an active agent added thereto.

5. The method of claim 4, wherein the polymer is ethylene vinyl alcohol copolymer and the solvent includes dimethylacetamide.

6. The method of claim 4, wherein the active agent is actinomycin D, paclitaxel, docetaxel, or rapamycin.

7. The method of claim 1, additionally comprising repeating the acts of applying and directing in sequence to form a coating of a desirable thickness or weight, wherein between each act there is a waiting period.

8. The method of claim 1, wherein the act of applying comprises using a nozzle to spray the composition onto the implantable device, wherein the distance from the tip of the nozzle to the outer surface of the implantable device is from about 0.5 cm to about 5.0 cm.

9. The method of claim 8, wherein the act of spraying is performed at a flow rate of about 0.01 mg/second to about 1.0 mg/second.

10. The method of claim 1, wherein the act of applying comprises spraying the composition onto the implantable device.

11. The method of claim 10, wherein the direction of the flow of the gas is substantially in the same direction as the composition spray.

12. The method of claim 10, wherein the direction of the flow of gas is at an angle relative to the direction of the composition spray.

13. The method of claim 10, wherein the direction of the flow of gas is substantially opposite to the direction of the composition spray.

14. A method of coating an implantable device comprising:
    applying a composition including a solvent to an implantable device; and
    directing a gas onto the implantable device, wherein if the solvent has a vapor pressure greater than 17.54 Torr at ambient temperature the temperature of the gas is adjusted to inhibit the evaporation of the solvent, and if the solvent has a vapor pressure of less than 17.54 Torr at ambient temperature the temperature of the gas is adjusted to induce the evaporation of the solvent, wherein the act of directing the gas is performed at a flow rate of about 300 feet/minute to about 10,000 feet/minute.

15. The method of claim 1, wherein the composition includes a radiopaque element or a radioactive isotope.

16. The method of claim 1, further comprising rotating the implantable device about an axis of the implantable device.

17. The method of claim 1, further comprising moving the implantable device in a linear direction along an axis of the implantable device.

18. The method of claim 1, wherein the implantable device is a stent and the stent is at least partially expanded during the acts of applying and directing.

19. The method of claim 1, wherein the gas is an inert gas.

20. The method of claim 1, wherein the gas is selected from a group of argon, nitrogen and air.

21. The method of claim 1, further comprising changing the temperature of the implantable device to a temperature other than ambient temperature.

22. A method of coating an implantable device comprising:
    applying a composition including a solvent to an implantable device; and
    actively directing a gas from a blower means onto the implantable device simultaneous with application of the composition to either induce or inhibit evaporation of the solvent from the composition to form a coating on the implantable device, wherein if the solvent is non-volatile the temperature of the gas is adjusted to induce the evaporation of the solvent, and if the solvent is volatile the temperature of the gas is adjusted to inhibit the evaporation of the solvent.

23. The method of claim 22, wherein if the solvent is volatile, the temperature of the gas is significantly less than the boiling temperature of the solvent.

24. The method of claim 22, wherein the temperature of the gas is about 25° C. to about 200° C. for the non-volatile solvent and is less than 25° C. for the volatile solvent.

25. The method of claim 22, further comprising, if the solvent is non-volatile increasing the temperature of the composition to a temperature above ambient temperature prior to application of the composition onto the implantable device, or alternatively, if the solvent is volatile decreasing the temperature of the composition to a temperature below ambient temperature prior to application of the composition onto the implantable device.

26. The method of claim 1, further comprising rotating the implantable device about an axis of the implantable device during the act of directing of the gas.

27. The method of claim 1, further comprising moving the implantable device in a linear direction across the blowing means during the act of directing of the gas.

28. The method of claim 1, wherein the implantable device is a stent, and further comprising both rotating the stent and moving the stent linearly across the blowing means during the act of directing of the gas.

29. The method of claim 1, wherein the gas is directed at the implantable device following a waiting period after the application of the composition to allow the composition sufficient time to flow and spread over the device before the solvent of the composition is removed.

30. The method of claim 1, wherein the temperature of the gas is 40° C. to 90° C.

* * * * *